United States Patent
Poddar et al.

(10) Patent No.: US 9,320,884 B2
(45) Date of Patent: Apr. 26, 2016

(54) METHOD AND SYSTEM FOR SWITCHING SHOCK VECTORS AND DECREASING TRANSTHORACIC IMPEDANCE FOR CARDIOVERSION AND DEFIBRILLATION

(71) Applicants: Piyush Poddar, Cranbury, NJ (US); Aaron Jiunhao Chang, Grand Prairie, TX (US); Melinda Chen, Lutherville, MD (US); Peter Malamas, Jamison, PA (US); Sandya Subramanian, Grand Rapids, MI (US); Todd J. Cohen, Port Washington, NY (US)

(72) Inventors: Piyush Poddar, Cranbury, NJ (US); Aaron Jiunhao Chang, Grand Prairie, TX (US); Melinda Chen, Lutherville, MD (US); Peter Malamas, Jamison, PA (US); Sandya Subramanian, Grand Rapids, MI (US); Todd J. Cohen, Port Washington, NY (US)

(73) Assignee: Nexus Control Systems, LLC, Port Washington, NY (US)

(*) Notice: Subject to any disclaimer, the term of this patent is extended or adjusted under 35 U.S.C. 154(b) by 0 days.

(21) Appl. No.: 14/102,967

(22) Filed: Dec. 11, 2013

(65) Prior Publication Data
US 2014/0163663 A1    Jun. 12, 2014

Related U.S. Application Data

(60) Provisional application No. 61/735,652, filed on Dec. 11, 2012.

(51) Int. Cl.
*A61N 1/39* (2006.01)
*A61N 1/04* (2006.01)

(52) U.S. Cl.
CPC .............. *A61N 1/0476* (2013.01); *A61N 1/046* (2013.01); *A61N 1/0492* (2013.01); *A61N 1/3918* (2013.01)

(58) Field of Classification Search
CPC ... A61N 1/0476; A61N 1/046; A61N 1/0492; A61N 1/3918
USPC ...................................... 607/5, 142
See application file for complete search history.

(56) References Cited

U.S. PATENT DOCUMENTS

| 6,065,154 A * | 5/2000 | Hulings et al. .................... 2/102 |
| 2005/0107834 A1* | 5/2005 | Freeman .............. A61N 1/3918 607/5 |
| 2012/0158075 A1* | 6/2012 | Kaib ...................... A61N 1/046 607/7 |

* cited by examiner

*Primary Examiner* — Theodore Stigell
*Assistant Examiner* — Michael Carey
(74) *Attorney, Agent, or Firm* — William Dippert; Laurence Greenberg; Werner Stemer

(57) ABSTRACT

A method and system improves the effectiveness of cardioversion or defibrillation through the ability to switch shock vectors and to reduce transthoracic impedance. An external multiple patch system comprises at least two options for a shocking vector once external patches are applied and adhered to desired locations on a patient's body. A manual switching mechanism in the system provides the ability to direct current from a defibrillator to either of two or more adhesive electrode patches. A method and system of decreasing transthoracic impedance comprises wrapping material around a patient's body to apply pressure to adhered patches, which further reduces transthoracic impedance by increasing effective pressure on the patches through use of pressure-focusing mechanisms located between a patch and a strap.

15 Claims, 4 Drawing Sheets

METHOD AND SYSTEM FOR SWITCHING SHOCK VECTORS AND DECREASING TRANSTHORACIC IMPEDANCE FOR CARDIOVERSION AND DEFIBRILLATION

CROSS-REFERENCE TO RELATED PATENT APPLICATION

This application is based upon and claims the benefit of the priority of U.S. Provisional Patent Application Ser. No. 61/735,652, filed Dec. 11, 2012, which is incorporated herein in its entirety.

FIELD OF THE INVENTION

This invention relates to devices used in cardioversion and defibrillation procedures. More particularly, this invention relates to devices and methods of directing shock vectors and reducing transthoracic impedance during cardioversion and defibrillation.

BACKGROUND OF THE INVENTION

Cardiac arrhythmias currently affect over 14 million individuals and claim the lives of 300,000 each year in the United States. Two common treatments for arrhythmia patients are cardioversion and defibrillation. In these treatments, clinicians deliver low-energy or high-energy electrical shocks to the heart to convert it to normal sinus rhythm. However, there is no guarantee that any given shock will work. If a given shock does not work, clinicians must make decisions, often in a matter of seconds, as to what to do to increase the chance of success on the next shock.

If the first shock fails, the current standard of care dictates that the only easily accessible option clinicians have is to increase the energy of the shock. However, this practice can cause unnecessary pain for the patient without ensuring increased success. According to the literature, less harmful but possibly equally effective alternatives, such as switching shock vectors or reducing transthoracic impedance, exist. Unfortunately, these alternatives are out of reach because there is no safe, standardized way to implement them quickly.

Over the years, there have been methods of switching shocking vectors for cardioversions and defibrillations, but there has been no method for applying a standardized pressure over the external patches being utilized. An example of relevant prior art is U.S. Published Patent Application No. 2006/0282124, which discloses methods that utilize transcutaneous cardioversion vectors, or those which require at least one internal cathode to produce a vector between an internal catheter and external electrode. However, the insertion of at least one internal catheter is more invasive than desired in some cases.

U.S. Pat. No. 4,554,928 discloses the "Booker Box," an electrophysiological switching unit that interconnects multiple electrode catheter leads, stimulator leads, and recorder channel leads. However, there are no standardized devices for simply switching between two shock vectors and reducing transthoracic impedance for external adhesive patches.

SUMMARY OF THE INVENTION

The present invention provides a novel device, system, and method for switching between shock vectors when utilizing external adhesive electrode patches while performing cardioversion or defibrillation. In addition, the device and system described herein may comprise one or more adjustable straps to apply pressure and to measure or standardize the application of pressure over the electrode patches during cardioversion or defibrillation.

A device useful according to the invention comprises three or more adhesive electrode patches, insulated wires extending from each adhesive electrode patch to a switching component, or switch, and insulated wires extending from the switching component to a connector. The connector is capable of connecting to a cardioverter/defibrillator, which comprises a control panel and a source of electrical energy. The device optionally comprises one or more adjustable straps that are capable of exerting pressure upon the adhesive patches.

The switching component comprises a switch, with an actuator, for switching between electrode patches. The switch preferably is FDA approved for defibrillation voltages and current loads. One example of a switch useful according to the invention is a switch identified as Part No. VD5AS00C-CZR00-000, available from Carling Technologies Inc., Plainville, Conn. The switch is preferably encased within an electrically insulated casing that isolates the body of the switch from the external environment. Wires from the adhesive electrode patches extend to the switch through holes on a first or proximal face of the switch casing, that is, the surface which faces the adhesive electrode patches when the device is configured in a typical layout. These wires are securely connected to the switch. Wires from a cardioverter/defibrillator connector extend into the switching component through holes in a second or distal surface of the switch casing, that is, the surface which faces the cardioverter/defibrillator connector when the device is configured in a typical layout. These wires are also securely connected to the switch.

Before shocking, an activator on the switch can be manipulated, preferably by hand, so that subsequently delivered current is directed between desired electrode patches. For delivery of cardioversion or defibrillation shock, current will travel through the cardioverter/defibrillator connector, through an actuating wire, into the switching mechanism, out to the desired adhesive electrode patch (referred to as the "actuator" patch) attached to a patient, and through the patient's body cavity. Then, the manually selected receiving adhesive electrode patch will conduct current from the patient's body cavity through the respective receiving wire through the proximal face of the switching component. This current passes through the switching component and back to the cardioverter/defibrillator connector via a receiving wire to complete the circuit between cardioverter/defibrillator and patient's body cavity. Before subsequent shocks, a user will be able to manually adjust the switch actuator to alter the shock vector, that is, to determine to which adhesive electrode patch the current will be directed, thus providing an alternative treatment in cardioversion or defibrillation.

The mechanism to provide measured and/or standardized pressure over electrode patches during shock delivery comprises at least one strip of material that can be embodied as a strap, elastic band, vest, non-compliant band, or any combination thereof. The mechanism is wrapped around a patient's body loosely and then tightened through a buckle or other clasping, connecting, or cinching mechanism to apply pressure. In one embodiment of the invention, a spacing or fulcrum, that is, pressure-focusing component is placed between a strap and one or more, preferably each, of the adhesive electrode patches. In another embodiment of the mechanism to apply standardized pressure, the mechanism utilizes a built-in insert in which to tuck the pressure-focusing component. The pressure-focusing component may comprise simply a block of rigid or semi-rigid material which provides a normal force to the patient body when placed between the patient and a strap. Optionally a pressure-focusing component comprises additional spring components which can be manually adjusted via various tightening mechanisms to quantify the force applied on the patient's body. Further, in other embodiments the mechanism of the pressure-focusing component comprises of an extension mechanism which functions similar to a car jack to provide an expanding force on both an electrode patch on a patient's body and a strap or belt when activated or operated. Prior to delivery of cardioversion or defibrillation shock, a strap or belt is tightened to a desired applied pressure, and secured, to push down on the pressure-focusing component and thus down on an adhesive electrode patch.

In another embodiment of the invention, to decrease transthoracic impedance, the tightening and applied force of a pressure-focusing component occurs as the cardioversion or defibrillation shock is applied. This increased pressure on the adhesive electrode patches, amplified by the action of the pressure-focusing components for at least the duration of the cardioversion or defibrillator shock, serves to reduce transthoracic impedance, thus improving electrical current delivery to the heart. Optionally the device comprises at least one electronic and/or mechanical sensor that provides feedback on the applied force from the tightening mechanism, which sensor or sensors can be incorporated into one or more pressure-focusing components.

In another embodiment of the invention, a device for performing cardioversion or defibrillation comprises:

three or more adhesive electrode patches for external application;

a switching mechanism in electrical connection with each adhesive electrode patch; and a cardioversion/defibrillator connector in electrical connection with the switching mechanism, wherein the switching mechanism has a switch to choose between at least two patches at a time.

In another embodiment of a device of the invention, the device comprises one or more straps capable of being adapted to increase pressure on one or more of the patches during use.

In another embodiment of a device of the invention, the strap is a strip of material with belt-like properties and/or elastic characteristics which wraps around a patient and/or hospital bed and/or table and has a connection mechanism with male and female connection components attached to either of two ends of said strip of material.

In another embodiment of a device of the invention, a tightening mechanism allows the application of eighteen or more pounds of force onto the adhesive electrode patches in a constant or transient manner.

In another embodiment of a device of the invention, a pressure-focusing component is attached to the strap and is positioned between at least one patch and the strap.

In another embodiment of a device of the invention, there are three pressure-focusing components.

In another embodiment of the invention, a system for performing cardioversion or defibrillation comprises:

three or more adhesive electrode patches;

a switching mechanism in electrical connection with each adhesive electrode patch;

a cardioversion/defibrillator connector in electrical connection with the switching mechanism; and a cardioverter or defibrillator, wherein the switching mechanism has a switch to choose between at least two patches at a time.

In another embodiment of a system of the invention, the switching mechanism is capable of and approved to handle common defibrillator voltage and current standards.

In another embodiment of the invention, in a method of performing cardioversion or defibrillation on a patient wherein adhesive electrode pads are applied to the patient's chest and/or back and/or side and electrical shocks are applied to the patient through the adhesive electrode pads, the improvement wherein there are at least three adhesive electrode patches and a switching mechanism can be used to direct current to at least two desired patches at a time.

In another embodiment of a method of the invention, the switching mechanism allows alternating the path of the cardioverter or defibrillator electrical current, through manual manipulation of switch user interface, between at least three external adhesive electrode patches, without need to lift electrodes from a patient's skin.

In another embodiment of the invention, a system for decreasing transthoracic impedance comprises:

a strip of material with belt-like properties and/or elastic characteristics or any combination thereof which wraps around patient and/or hospital bed and/or table and a contiguous connection on said strip of material and/or a connection mechanism on said strip of material with male and female connection components attached to either of two ends of said strip of material;

a tightening mechanism which allows the customized application of eighteen or more pounds of force onto the desired adhesive electrode patches in a constant or transient manner.

a plurality of pressure-focusing mechanisms wherein said mechanisms embody fitted blocks of material and/or blocks of material capable of extending force against a desired patch and said strip of material with various adjustable screw and/or pneumatic and/or hydraulic mechanisms or any combination thereof, and/or soft or rigid inserts filled with filling material or mechanisms which are positioned over desired electrode patches and under said strip of material; and a mechanism of accommodating said pressure-focusing mechanisms to the strip of material.

In another embodiment of a system of the invention, a system comprises VELCRO inserts and/or physical congruency and/or an alternate mechanical mechanism.

In another embodiment of a system of the invention, a mechanism incorporated into the pressure-focusing mechanism provides qualitative and/or quantitative feedback on the pressure being applied on desired electrode patches.

In another embodiment of a system of the invention, the pressure-focusing mechanisms comprise sand and/or spring mechanisms or any combination thereof.

Still further advantages of the present invention will be appreciated to those of ordinary skill in the art upon reading and understanding the following detailed description. Therefore, it should now be apparent that the invention substantially achieves all the above aspects and advantages. Additional aspects and advantages of the invention will be set forth in the description that follows, and in part will be inherent from the description, or may be appreciated by practice of the invention. Moreover, the aspects and advantages of the invention may be realized and obtained by means of the instrumentalities and combinations particularly pointed out in the appended claims.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts. The drawings are only for purposes of illustrating the preferred embodiments and are not to be construed as limiting the invention.

DETAILED DESCRIPTION OF THE INVENTION

Figure 1:
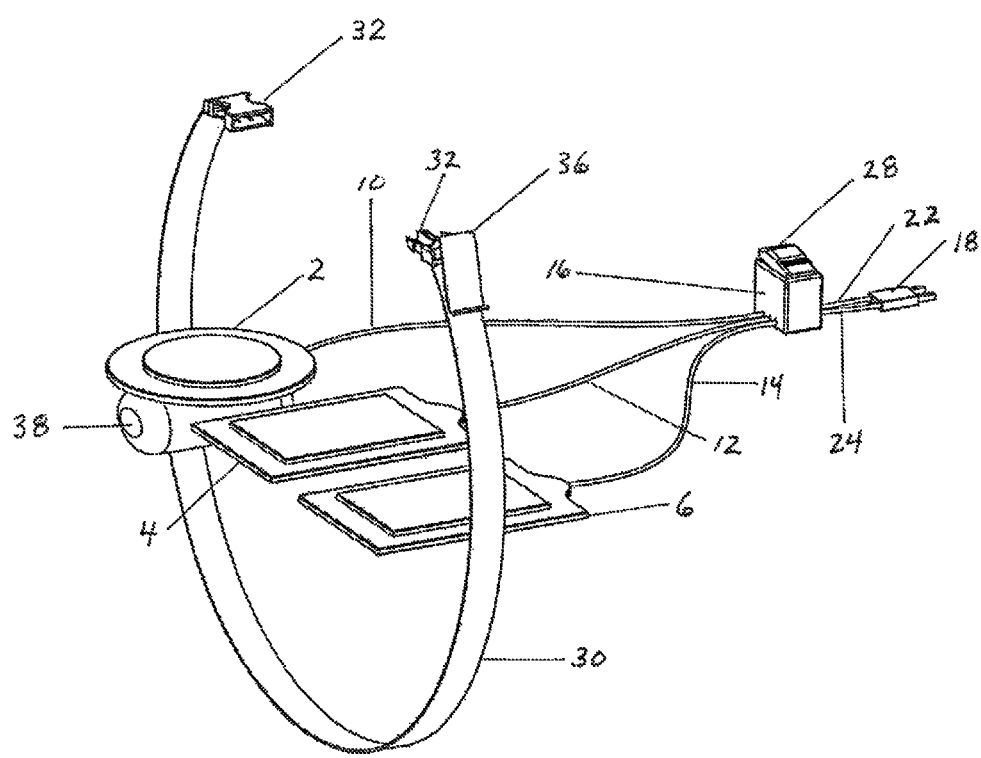
FIG. 1 is schematic representation of an embodiment of the invention.

The present invention, in the various embodiments described herein, relates to a device, system, and method to direct shock vectors and reduce transthoracic impedance during cardioversion or defibrillation. The invention can perhaps be better understood from the drawings. With regard to FIG. 1, there is a representation of a typical layout of an embodiment of the invention. Here there are three adhesive electrode patches, an actuator patch 2 that would be placed on a patient's chest, and receiver patches 4 and 6 that would be positioned on the patient's back. Patches 2, 4, 6 are connected through insulated wires 10, 12, 14, respectively, to a switch (not shown) within switch casing 16. Also, patches 2, 4, 6 can have any desired or conventional or practical shape or size. A cardioverter/defibrillator connector 18 is connected via actuating wire 22 and receiving wire 24 to the switch within switch casing 16. Switch casing 16 has an actuator 28 for activating the switch.

A strap 30 with a buckle or connector 32 and a method of tightening or cinch 36 is loosely arranged around patches 2, 4, 6 in this representation. An exemplary pressure-focusing component 38 is positioned beneath patch 2. The tightening of strap 30 with a connector 32 and cinch 36 across pressure-focusing component 38 can reduce transthoracic impedance.

Figure 2:
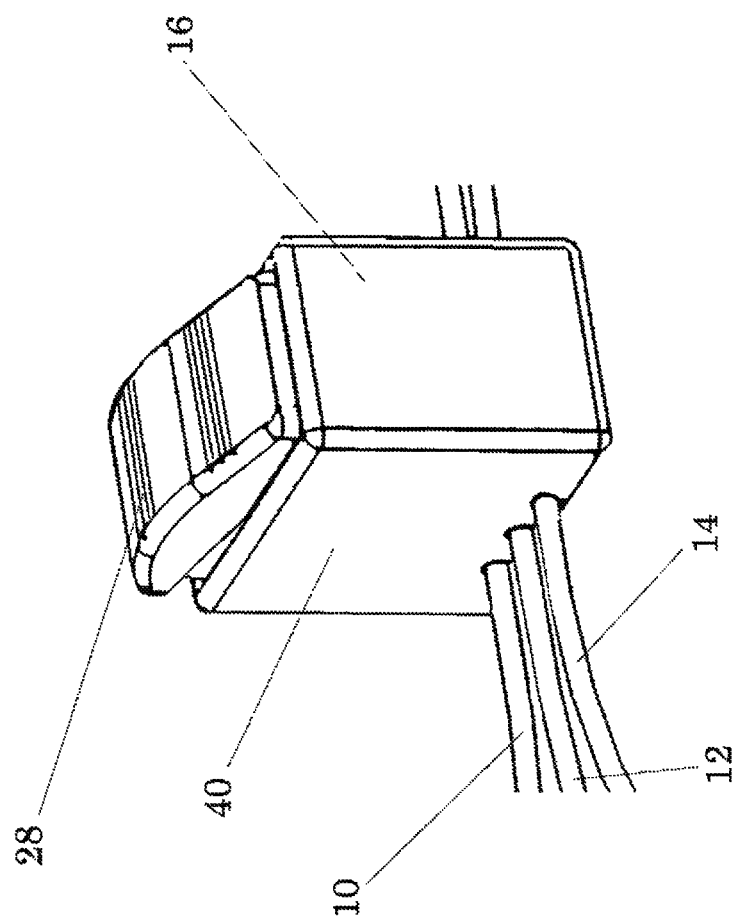
FIG. 2 is a schematic representation of an oblique view of a switching component useful according to the invention.

FIG. 2 is a close up view of a proximal surface 40 of switch casing 16. Wire 10 from actuator patch 2, wire 12 from receiver patch 4, and wire 14 from receiver patch 6 all enter the switch casing 16 through a plurality of holes 44 on proximal surface 40. Furthermore, it can be seen that the switching mechanism is in one of two positions as dictated by the rocker style of actuator 28.

Figure 3:
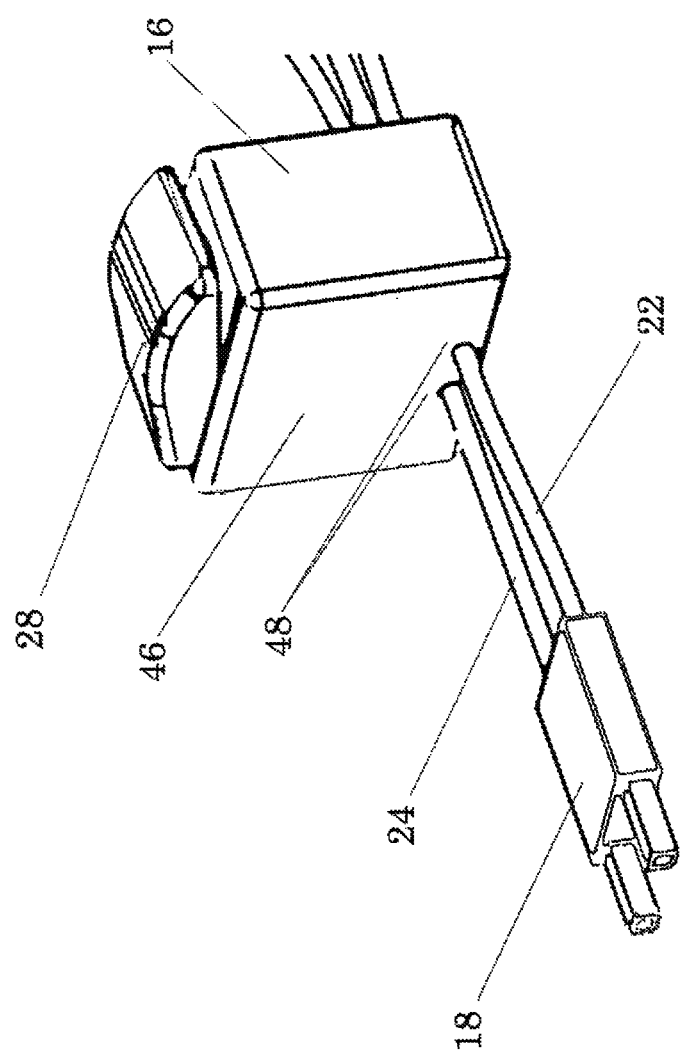
FIG. 3 is a schematic representation of a rear oblique view of a switching component with a cardioverter/defibrillator connector useful according to the invention.

A distal surface 46 of switch casing 16 can be seen in FIG. 3. Actuating wire 22 and receiving wire 24 extending from cardioversion/defibrillator connector 18 enter switch casing 16 through a plurality of holes 48 on distal surface 46.

Figure 4:
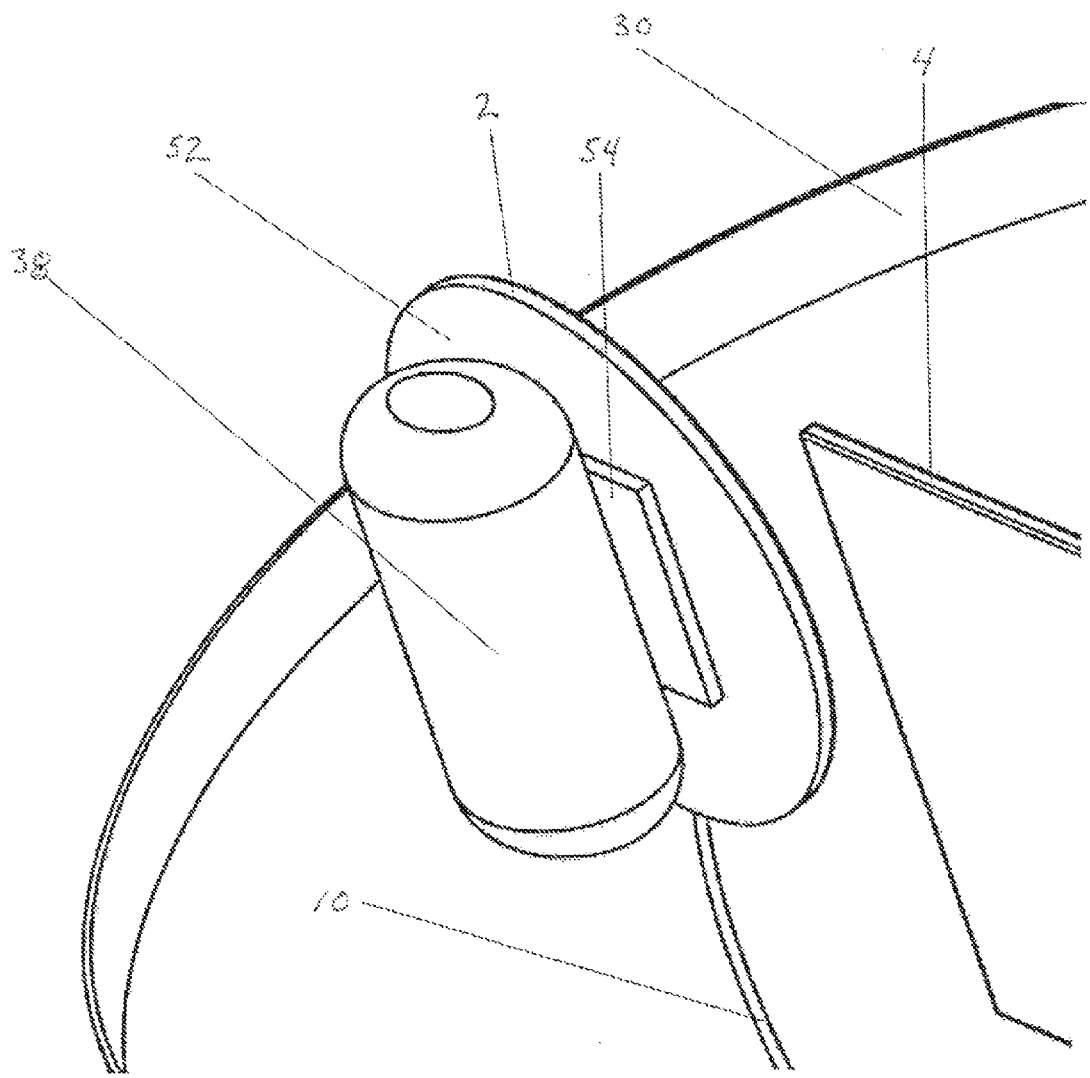
FIG. 4 is a schematic representation of a view of a pressure-focusing component adjacent to an adhesive electrode patch according to the invention.

As can be seen in FIG. 4, pressure-focusing component 38, which has an implicit force sensing mechanism, is attached to the non-adhesive side 52 of actuator patch 2. This attachment is achieved through a VELCRO-type strip 54 on the non-adhesive side 52 and cooperating hooks or loops on pressure-focusing component 38.

A preferred embodiment of the invention comprises using an additional adhesive electrode patch to the conventional two electrode patches in methods and systems for cardioversion or defibrillations as well as a switching mechanism into which the wires are fed to allow switching between two different shock vectors. In operation of the preferred embodiment, the user would first lay out the strap mechanism on a flat and stable surface, such as a hospital bed or the ground. Next, the user would apply the external adhesive electrode patches to the desired locations on the patient. In the conventional use, the actuator patch would be placed in the canonical antero position, and the two receiver patches would be placed in the canonical lateral and posterior positions. Then, the user would place the pressure-focusing components on top of the desired patches and attachment between the pressure-focusing components and patches would be achieved via a VELCRO-type mechanism. Next, the strap mechanism is placed around the patient, and the buckle of the strap mechanism is connected. Then, the user would tighten the strap using the provided tightening mechanism built into the strap to achieve the desired pressure applied to the patient body cavity.

The user would then toggle the manual switching mechanism to deliver a shocking vector between the actuator patch and the desired receiver patch. With the defibrillator connected to the defibrillator connector, the user would then deliver a defibrillation shock according to standard defibrillator manufacturer recommended practices. The tightening mechanism would synchronously allow maximal force on the desired electrode patches only upon the duration of defibrillation. Upon analysis of shocking effect on patient arrhythmia, the decision can be made whether to remove the device and end the cardioversion or defibrillation procedure upon restoration of normal sinus rhythm, or to toggle the manual switch into the alternate position to deliver a subsequent shock via the shocking vector between the actuator patch and the other receiver patch. After switching the shock vector, the same process of delivering a standard defibrillation shock is repeated. This method of switching and shocking can be carried out until a successful or terminal result as defined by the user is achieved.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to he considered as limited by the foregoing description but is only limited by the scope of the appended claims.

We claim:

1. A device for performing cardioversion or defibrillation, which comprises:
   a first adhesive electrode patch for external application of an electrical shock to the chest of a patient;
   second and third adhesive electrode patches to be applied to the back or back and a side of the patient, only one of which at a time can receive a shock vector from the first adhesive electrode patch;
   a manual switching mechanism in electrical connection with each adhesive electrode patch; and
   a cardioversion/defibrillator connector in electrical connection with the switching mechanism,
   wherein the switching mechanism has a switch to choose which of the second and third receiver adhesive electrode patches will receive the shock vector.

2. The device of claim 1, which comprises one or more straps capable of being adapted to increase pressure on one or more of the adhesive electrode patches during use.

3. The device of claim 2, wherein the strap is a strip of material with belt-like properties and/or elastic characteristics which wraps around a patient and/or hospital bed and/or table and has a connection mechanism with male and female connection components attached to either of two ends of said strip of material.

4. The device of claim 3, wherein a tightening mechanism allows the application of eighteen or more pounds of force onto the adhesive electrode patches in a constant or transient manner.

5. The device of claim 2, wherein a pressure-focusing component is attached to the strap and is positioned between at least one adhesive electrode patch and the strap.

6. The device of claim 3, wherein there are three pressure-focusing components to focus pressure on each of the adhesive electrode patches.

7. A system for performing cardioversion or defibrillation, which comprises:
   a first adhesive electrode patch for external application of an electrical shock to the chest of a patient;
   second and third receiver adhesive electrode patches to be applied to the back or back and a side of the patient, only one of which at a time can receive a shock vector from the first adhesive electrode patch;
   a manual switching mechanism in electrical connection with each adhesive electrode patch;
   a cardioversion/defibrillator connector in electrical connection with the switching mechanism; and
   a cardiovertor or defibrillator,
   wherein the switching mechanism has a switch to choose which of the second and third adhesive electrode patches will receive the shock vector.

8. The system of claim 7, wherein the switching mechanism is capable of and approved to handle common defibrillator voltage and current standards.

9. In a method of performing cardioversion or defibrillation on a patient wherein adhesive electrode pads are applied to the patient's chest and back or back and a side and electrical shocks are applied to the patient through the adhesive electrode pads, the improvement wherein there are a first adhesive electrode patch for external application of an electrical shock to the chest of a patient and second and third adhesive electrode patches to be applied to the back or back and a side of the patient, only one of which at a time can receive a shock vector from the first adhesive electrode patch and a manual switching mechanism can be used to direct current to choose which of the second and third adhesive electrode patches will receive the shock vector.

10. The method of claim 9, wherein the switching mechanism allows alternating the path of the cardioverter or defibrillator electrical current, through manual manipulation of switch user interface, between a first adhesive electrode patch and one of second and third adhesive electrode patches, without need to lift electrodes from a patient's skin.

11. A system for decreasing transthoracic impedance comprising:
   a strip of material with belt-like properties and/or elastic characteristics or any combination thereof which wraps around patient and/or hospital bed and/or table and a contiguous connection on said strip of material and/or a connection mechanism on said strip of material with male and female connection components attached to either of two ends of said strip of material;
   a tightening mechanism which allows the customized application of eighteen or more pounds of force onto the desired adhesive electrode patches in a constant or transient manner;
   a plurality of pressure-focusing mechanisms wherein said mechanisms embody fitted blocks of material and/or blocks of material capable of extending force against a desired patch and said strip of material with various adjustable screw and/or pneumatic and/or hydraulic mechanisms or any combination thereof, and/or soft or rigid inserts filled with filling material or mechanisms which are positioned over desired electrode patches and under said strip of material; and
   a mechanism of accommodating said pressure-focusing mechanisms to said strip of material.

12. The system of claim 11 which may comprise VELCRO inserts and/or physical congruency and/or an alternate mechanical mechanism.

13. The system of claim 11, wherein a mechanism incorporated into the pressure-focusing mechanism provides qualitative and/or quantitative feedback on the pressure being applied on desired electrode patches.

14. The system of claim 11, wherein the pressure-focusing mechanisms comprise sand and/or spring mechanisms or any combination thereof.

15. A device for performing cardioversion or defibrillation, which comprises:
   a first adhesive electrode patch for external application of an electrical shock to the chest of a patient;
   second and third adhesive electrode patches to be applied to the back or back and a side of the patient, only one of which at a time can receive a shock vector from the first adhesive electrode patch;
   a manual switching mechanism in electrical connection with each adhesive electrode patch, wherein the switching mechanism has a switch to choose which of the second and third adhesive electrode patches will receive the shock vector;
   a cardioversion/defibrillator connector in electrical connection with the switching mechanism;
   one or more straps capable of being adapted to increase pressure on one or more of the adhesive electrode patches during use; and
   a tightening mechanism allows the application of eighteen or more pounds of force onto the adhesive electrode patches in a constant or transient manner,
   wherein a pressure-focusing component is attached to at least one of the one or more straps and is positioned between at least one adhesive electrode patch and the strap.

* * * * *